US009315563B2

(12) United States Patent
Wu et al.

(10) Patent No.: US 9,315,563 B2
(45) Date of Patent: Apr. 19, 2016

(54) PEPTIDES THAT INHIBIT ANGIOTENSIN CONVERTING ENZYME AND PEPTIDES WITH ANTIOXIDANT ACTIVITY PURIFIED FROM OVOTRANSFERRIN AND METHODS OF PRODUCING AND USING THE SAME

(75) Inventors: Jianping Wu, Edmonton (CA); Kaustav Majumder, Edmonton (CA)

(73) Assignee: The Governors of the University of Alberta, Edmondton, Alberta (CA)

( * ) Notice: Subject to any disclaimer, the term of this patent is extended or adjusted under 35 U.S.C. 154(b) by 0 days.

(21) Appl. No.: 13/256,839

(22) PCT Filed: Mar. 19, 2010

(86) PCT No.: PCT/IB2010/000829
§ 371 (c)(1),
(2), (4) Date: Jan. 20, 2012

(87) PCT Pub. No.: WO2010/106437
PCT Pub. Date: Sep. 23, 2010

(65) Prior Publication Data
US 2013/0116183 A1 May 9, 2013

Related U.S. Application Data

(60) Provisional application No. 61/161,901, filed on Mar. 20, 2009.

(51) Int. Cl.
*A61K 38/55* (2006.01)
*C12P 21/06* (2006.01)
*C07K 14/79* (2006.01)
*A23J 3/34* (2006.01)
*A23L 1/305* (2006.01)
*C07K 1/113* (2006.01)
*C07K 5/083* (2006.01)
*C07K 5/097* (2006.01)
*C07K 5/103* (2006.01)
*C07K 5/117* (2006.01)
*A61K 38/00* (2006.01)

(52) U.S. Cl.
CPC . *C07K 14/79* (2013.01); *A23J 3/34* (2013.01); *A23L 1/3053* (2013.01); *C07K 1/1133* (2013.01); *C07K 5/0808* (2013.01); *C07K 5/0821* (2013.01); *C07K 5/101* (2013.01); *C07K 5/1008* (2013.01); *C07K 5/1024* (2013.01); *C12P 21/06* (2013.01); *C12Y 304/15001* (2013.01); *A61K 38/00* (2013.01); *Y02P 20/52* (2015.11)

(58) Field of Classification Search
CPC ......... A23J 3/34; A23L 1/3053; A61K 38/00; C07K 14/79; C07K 1/1133; C07K 5/0808; C07K 5/0821; C07K 5/1008; C07K 5/101; C07K 5/1024; C12P 21/06; C12Y 304/15001
See application file for complete search history.

(56) References Cited

U.S. PATENT DOCUMENTS

2009/0029005 A1 *  1/2009  Van Amerongen et al. .... 426/63

FOREIGN PATENT DOCUMENTS

JP           11343297      * 12/1999

OTHER PUBLICATIONS

Wu et al. Food Res Int'l. 46;480-487:2012.*
ExPASy. www.expasy.org. This databased was used to show a Pepsin digest (Pn2) of Ovotransferrin (P02789).*
International Search Report dated Aug. 9, 2010 for international application No. PCT/IB/2010/000829.
Majumder et al., "Angiotensin I Converting Enzyme Inhibitory Peptides from Simulated in Vitro Gastrointestinal Digestion of Cooked Eggs", Journal of Agriculture and Food Chemistry, 2009, vol. 57, pp. 471-477, American Chemical Society, USA.
Wu et al., "Structural Requirements of Angiotensin I-Converting Enzyme Inhibitory Peptides: Quantitative Structure-Activity Relationship Study of Di- and Tripeptides", Journal of Agriculture and Food Chemistry, 2006, vol. 54, pp. 732-738, American Chemical Society.
Davalos et al., "Antioxidant Activity of Peptides Derived from Egg White Proteins by Enzymatic Hydrolysis", Journal of Food Production, 2004, vol. 67, pp. 1939-1944, Intl Association for Food Production.
Lee et al., "One Peptide Derived from Hen Ovotransferrin as Prodrug to Inhibi Angiotensin Converting Enzyme", Journal of Food and Drug Analysis, 2006, vol. 14, pp. 31-35.
Lee et al., "Antihypertensive Effect of Angiotensin-Converting Enzyme Inhibitory Peptide Obtained for Hen Ovotransferrin", Journal of the Chinese Chemical Society, 2006, vol. 53, pp. 495-501.
Majumder, Kaustav, "QSAR-Aided Study of Anthiypertensive Peptides From Egg Protiens", Misc Thesis, University of Alberta. 2009.
Williams et al., "The iron-binding properties of hen ovotransferrin," 1978, Biochem J., 173:535-542.
Sipola et al., "Effect of long-term intake of milk products on blood pressure in hypertensive rats," 2002, J. Dairy Res., 69:103-111.
Maruyama et al., "A peptide inhibitor of angiotensin I converting enzyme in the tryptic hydrolysate of casein," 1982, Agric. Biol. Chem., 46:1393-1394.
Majumder et al., "Egg-derived ACE-inhibitory peptides IQW and LKP reduce blood pressure in spontaneously hypertensive rats," 2015, J. Functional Foods, 13:50-60.
Majumder et al., "Egg-derived tri-peptcle IRW exerts antihypertensive effects in spontaneously hypertensive rats," 2013, PLOS One, 9:e82829.

* cited by examiner

Primary Examiner — Amber D Steele
Assistant Examiner — Schuyler Milton
(74) Attorney, Agent, or Firm — Gardner Groff Greenwald & Villanueva, PC

(57) ABSTRACT

Described herein are methods of identifying and releasing bioactive peptides from ovotransferrin The method involves (a) contacting ovotransferrin with a reducing agent, a sonication step, a high pressure processing step, a heating step, a fermentation step, or any combination thereof, and (b) contacting the ovotransferrin after step (a) with a hydrolytic enzyme to produce bioactive peptides that exhibit angiotensin converting enzyme inhibitory activity or antioxidant activity when compared to the parent protein. The bioactive peptides may be added to foodstuffs, a medication, or to any potable, ingestible, or edible compositions.

19 Claims, 3 Drawing Sheets

SEQUENCE LISTING

<160> NUMBER OF SEQ ID NOS: 24

<210> SEQ ID NO 1
<211> LENGTH: 3
<212> TYPE: PRT
<213> ORGANISM: Artificial Sequence
<220> FEATURE:
<223> OTHER INFORMATION: Synthetic Construct

<400> SEQUENCE: 1

Ile Arg Trp
1

```
<210> SEQ ID NO 2
<211> LENGTH: 3
<212> TYPE: PRT
<213> ORGANISM: Artificial Sequence
<220> FEATURE:
<223> OTHER INFORMATION: Synthetic Construct

<400> SEQUENCE: 2

Ile Gln Trp
1

<210> SEQ ID NO 3
<211> LENGTH: 3
<212> TYPE: PRT
<213> ORGANISM: Artificial Sequence
<220> FEATURE:
<223> OTHER INFORMATION: Synthetic Construct

<400> SEQUENCE: 3

Leu Lys Pro
1

<210> SEQ ID NO 4
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: X is deaminated Asp

<400> SEQUENCE: 4

Ile Ala Xaa Asn Glu Ala Asp Ala Ile Ser Leu Asp Gly Gly Gln Val
1               5                   10                  15

Phe Glu Ala Gly
            20

<210> SEQ ID NO 5
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (9)..(9)
<223> OTHER INFORMATION: X is oxidized His

<400> SEQUENCE: 5

Pro Ile Ala Ala Glu Val Tyr Glu Xaa Thr Glu Gly Ser Thr Thr Ser
1               5                   10                  15

Tyr

<210> SEQ ID NO 6
<211> LENGTH: 16
<212> TYPE: PRT
<213> ORGANISM: Artificial Sequence
<220> FEATURE:
<223> OTHER INFORMATION: Synthetic Construct

<400> SEQUENCE: 6

Ile Ala Ala Glu Val Tyr Glu His Thr Glu Gly Ser Thr Thr Ser Tyr
1               5                   10                  15

<210> SEQ ID NO 7
```

```
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Ala Gly Trp Asn Ile Pro Ile Gly Thr
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Construct

<400> SEQUENCE: 8

Ala Gly Trp Asn Ile Pro
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct

<400> SEQUENCE: 9

Ala Gly Trp Asn Ile
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic Construct

<400> SEQUENCE: 10

Trp Asn Ile Pro
1

<210> SEQ ID NO 11
<211> LENGTH: 15
<212> TYPE: PRT
<213> ORGANISM: Artificial Sequence
<220> FEATURE:
<223> OTHER INFORMATION: Synthetic Construct

<400> SEQUENCE: 11

Ala Ile Glu Trp Glu Gly Ile Glu Ser Gly Ser Val Glu Gln Ala
1               5                   10                  15

<210> SEQ ID NO 12
<211> LENGTH: 14
<212> TYPE: PRT
<213> ORGANISM: Artificial Sequence
<220> FEATURE:
<223> OTHER INFORMATION: Synthetic Construct

<400> SEQUENCE: 12

Ile Glu Trp Glu Gly Ile Glu Ser Gly Ser Val Glu Gln Ala
1               5                   10

<210> SEQ ID NO 13
<211> LENGTH: 9
```

```
<212> TYPE: PRT
<213> ORGANISM: Artificial Sequence
<220> FEATURE:
<223> OTHER INFORMATION: Synthetic Construct

<400> SEQUENCE: 13

Leu Ser Lys Ala Gln Ser Asp Phe Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Construct

<400> SEQUENCE: 14

Leu Gly Phe Glu Tyr
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic Construct

<400> SEQUENCE: 15

Leu Gly Phe Glu Tyr Tyr
1               5

<210> SEQ ID NO 16
<211> LENGTH: 10
<212> TYPE: PRT
<213> ORGANISM: Artificial Sequence
<220> FEATURE:
<223> OTHER INFORMATION: Synthetic Construct

<400> SEQUENCE: 16

Leu Val Glu Lys Gly Asp Val Ala Phe Ile
1               5                   10

<210> SEQ ID NO 17
<211> LENGTH: 5
<212> TYPE: PRT
<213> ORGANISM: Artificial Sequence
<220> FEATURE:
<223> OTHER INFORMATION: Synthetic Construct

<400> SEQUENCE: 17

Ile Leu Glu Leu Pro
1               5

<210> SEQ ID NO 18
<211> LENGTH: 4
<212> TYPE: PRT
<213> ORGANISM: Artificial Sequence
<220> FEATURE:
<223> OTHER INFORMATION: Synthetic Construct

<400> SEQUENCE: 18

Ile Leu Glu Leu
1

<210> SEQ ID NO 19
<211> LENGTH: 20
<212> TYPE: PRT
```

```
<213> ORGANISM: Artificial Sequence
<220> FEATURE:
<223> OTHER INFORMATION: Synthetic Construct

<400> SEQUENCE: 19

Ile Ala Asn Asn Glu Ala Asp Ala Ile Ser Leu Asp Gly Gly Gln Val
1               5                   10                  15

Phe Glu Ala Gly
            20

<210> SEQ ID NO 20
<211> LENGTH: 17
<212> TYPE: PRT
<213> ORGANISM: Artificial Sequence
<220> FEATURE:
<223> OTHER INFORMATION: Synthetic Construct

<400> SEQUENCE: 20

Pro Ile Ala Ala Glu Val Tyr Glu His Thr Glu Gly Ser Thr Thr Ser
1               5                   10                  15

Tyr

<210> SEQ ID NO 21
<211> LENGTH: 6
<212> TYPE: PRT
<213> ORGANISM: Artificial Sequence
<220> FEATURE:
<223> OTHER INFORMATION: Synthetic Construct

<400> SEQUENCE: 21

Val Ile Pro Met Gly Leu
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic Construct

<400> SEQUENCE: 22

Gly Trp Asn Ile Pro
1               5

<210> SEQ ID NO 23
<211> LENGTH: 4
<212> TYPE: PRT
<213> ORGANISM: Artificial Sequence
<220> FEATURE:
<223> OTHER INFORMATION: Synthetic Construct

<400> SEQUENCE: 23

Gly Trp Asn Ile
1

<210> SEQ ID NO 24
<211> LENGTH: 3
<212> TYPE: PRT
<213> ORGANISM: Artificial Sequence
<220> FEATURE:
<223> OTHER INFORMATION: Synthetic Construct

<400> SEQUENCE: 24

Trp Asn Ile
1
```

PEPTIDES THAT INHIBIT ANGIOTENSIN CONVERTING ENZYME AND PEPTIDES WITH ANTIOXIDANT ACTIVITY PURIFIED FROM OVOTRANSFERRIN AND METHODS OF PRODUCING AND USING THE SAME

CROSS REFERENCE TO RELATED APPLICATIONS

This application claims priority upon U.S. provisional application Ser. No. 61/161,901, filed Mar. 20, 2009. This application is hereby incorporated by reference in its entirety.

BACKGROUND

Bioactive peptides are specific fragments of proteins that are thought to have certain physiological benefits for human health. Bioactive peptides are latent in intact proteins but can be released through in vitro or in vivo enzymatic hydrolysis from the parent food proteins. For example, milk has been identified to contain numerous bioactive proteins and peptides. Such bioactive proteins include lactoferrin, caseins, colostrums, and praventin. See Maruyama, S.; Mitachi, H.; Tanaka, H.; Tomizuka, N.; Suzuki, H. Studies on the active site and antihypertensive activity of angiotensin I-converting enzyme inhibitors derived from casein. *Agricultural Biological Chemistry* 1998, 51, 1581-1586; FitzGerald, R. J.; Murray, B. A.; Walsh, D J. Hypotensive peptides from milk proteins. *Journal of Nutrition* 2004, 134, 980S-988S; which is hereby incorporated by reference in its entirety. It is speculated that these peptides have an antihypertensive effect and play a role in reducing or inhibiting the Angiotensin Converting Enzyme (ACE).

Angiotensin converting enzyme (ACE) is the key enzyme responsible for the regulation of blood pressure through rennin-angiotensin system. ACE catalyses the formation of angiotensin II, a potent vasoconstrictor, from angiotensin I and inactivates bradykinin, a vasodilator. Elevated activity of ACE could lead to a higher level of angiotensin II and therefore cause high blood pressure or hypertension. Inhibition of ACE is a therapeutic strategy for antihypertension drug development. Currently, ACE inhibitory drugs are the first line therapy of hypertension. Although synthetic ACE inhibitors, such as captopril and enalapril, are widely used as anti-hypertensive drugs, they inevitably cause adverse side effects including chronic coughing and angioedima.

In addition to milk proteins, egg proteins are thought to be a rich source of bioactive proteins and bioactive peptides. Egg proteins are one of the major sources of dietary nitrogen. In egg, proteins are distributed throughout both the egg white and yolk. It is theorized that proteins within egg have numerous biological activities including antimicrobial activity, anticancer activity, and protease inhibition, and it is further thought that egg proteins are an excellent source of bioactive peptides including antihypertensive peptides.

For example, ovotransferrin is one of the major proteins in egg white, accounting for approximately 13% of the overall protein in egg white. However, due to ovotransferrin's amino acid sequence (i.e. having high sulfur content and numerous disulfide bridges), native ovotransferrin is resistant to heat and enzymatic hydrolysis. Therefore, it is generally difficult to convert naturally occurring proteins into bioactive peptides that possess health benefits.

SUMMARY

Described herein are methods of identifying and releasing bioactive peptides from their full length proteins. The method involves (a) contacting the protein with a reducing agent, a sonication step, a high pressure processing step, a heating step, a fermentation step, or any combination thereof; and (b) contacting the protein after step (a) with a hydrolytic enzyme to produce the bioactive peptide. The bioactive peptides exhibit enhanced biological activity when compared to the parent protein. The bioactive peptides may be added to foodstuffs, a medication, or to any potable, ingestible, or edible compositions.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
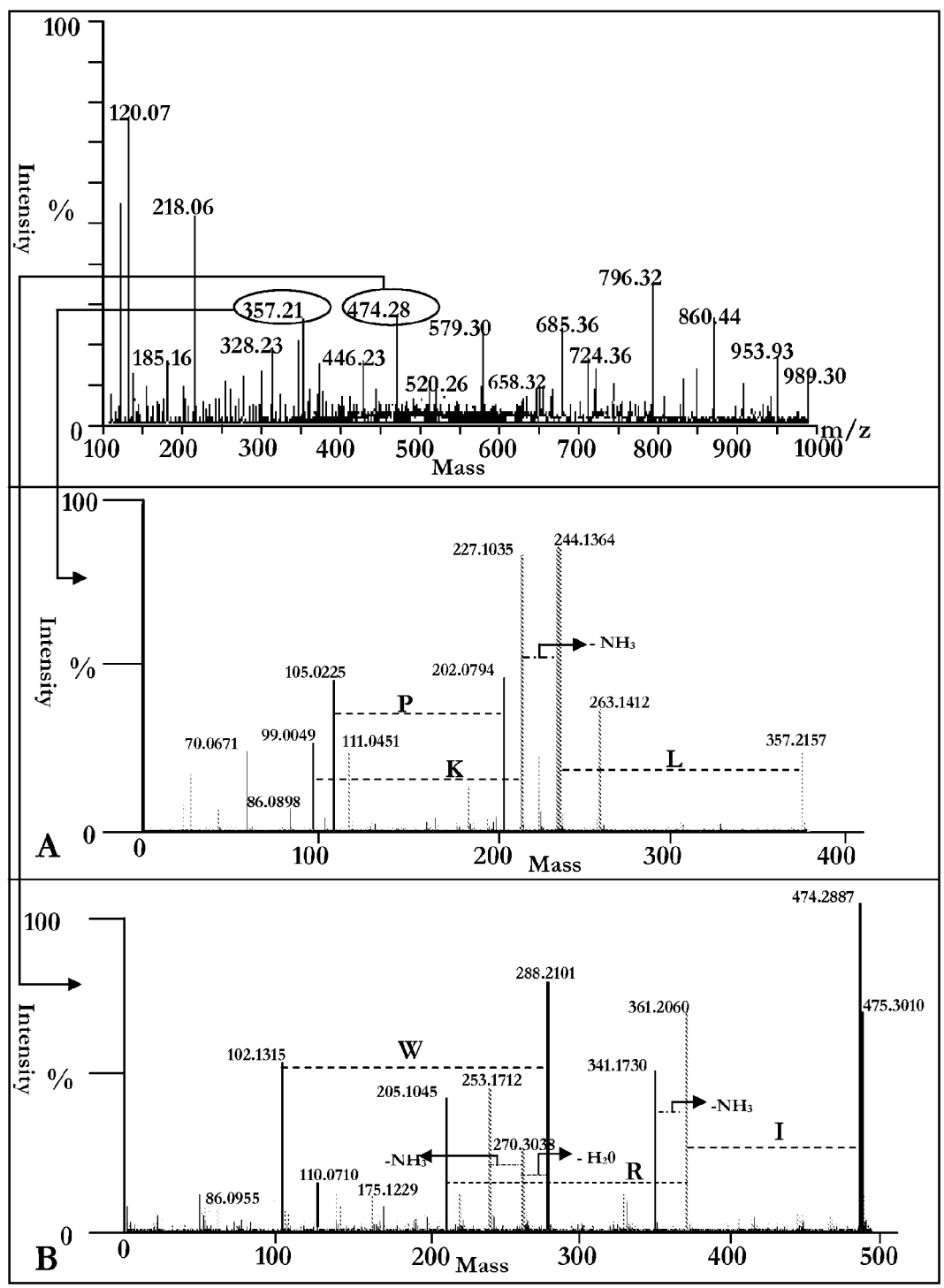
FIG. 1 shows MS peaks of ovotransferrin hydrolysate after sonication-aided enzymatic treatment. Two bioactive peptides LKP (SEQ ID NO:3) and IRW (SEQ ID NO:1) were de novo sequenced using their MS-MS spectrum by monisotopic mass of the amino acids.

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a bioactive peptide" includes mixtures of two or more such bioactive peptides, and the like.

"Optional" or "optionally" means that the subsequently described event or circumstance can or cannot occur, and that the description includes instances where the event or circumstance occurs and instances where it does not.

As used herein, "subject" refers to a mammal, including a human that benefits from the compositions and methods described herein.

As used herein, the term "bioactive peptide" may be used to refer to a natural or synthetic molecule comprising two or more amino acids linked by the carboxyl group of one amino acid to the alpha amino group of another. A bioactive peptide is a peptide that is released from a naturally occurring protein after treatment by the methods described herein. Alternatively, a bioactive peptide may include a chemically synthesized peptide which has similar properties to the bioactive peptide generated from the methods described herein.

As used herein, the term "isolated," with respect to peptides, refers to material that has been removed from its original environment, if the material is naturally occurring. For example, a naturally-occurring protein or peptide present in a living animal is not isolated, but the same peptide, which is separated from some or all of the coexisting materials in the natural system, is isolated. Such isolated peptide could be part of a composition and still be isolated in that the composition is not part of its natural environment. An "isolated" peptide may include material that is synthesized or produced by recombinant DNA technology.

As used herein the term "protein hydrolysate" refers to a peptide (e.g. a bioactive peptide) that results from the enzymatic digestion (i.e. enzyme hydrolysis) of a protein or fermentation of a protein.

As used herein, the term "about" is used to provide flexibility to a numerical range endpoint by providing that a given value may be "a little above" or "a little below" the endpoint without affecting the desired result.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Described herein are methods of identifying and releasing bioactive peptides from their full length proteins. Bioactive peptides may include specific fragments of proteins that are thought to have certain physiological benefits for human health. These bioactive peptides may have therapeutic properties such as, for example, lowering blood pressure and may be added to foodstuffs, a medication, or to any potable, ingestible, or edible compositions. Generally, bioactive peptides are latent in intact proteins but can be released through in vitro or in vivo enzymatic hydrolysis from the parent food proteins. However, enzymatic hydrolysis of certain proteins may be problematic due to amino acid consistency. For example, proteins with high sulphur content and with numerous disulfide bridges may be resistant to enzymatic hydrolysis or only allow for incomplete hydrolysis. Due to this incomplete digestion, bioactive peptides may not be released from certain proteins.

To more efficiently release bioactive peptides from proteins that may be resistant or only allow for incomplete enzymatic hydrolysis, a more efficient method is needed. In one aspect, methods for producing a bioactive peptide from a protein, as the ones discussed above, include (a) contacting the protein with a reducing agent, a sonication step, a high pressure processing step, a heating step, a fermentation step, or any combination thereof; and (b) contacting the protein after step (a) with a hydrolytic enzyme to produce the bioactive peptide. In this aspect, the protein may be subjected to a reducing agent or a sonication step individually or in combination. When the protein is subjected to a reducing agent and sonication step, this may occur either sequentially in any order or simultaneously.

The proteins that can be subjected to the methods described herein may include many naturally occurring or recombinant proteins. In one aspect, the proteins can be in either a liquid solution or a solid form (i.e. powder form, gelatinous form, etc.) and can have one or more disulfide bridges that may be subjected to the methods described herein. In this aspect, plant proteins such as, for example, soybean proteins, canola proteins, pea proteins, flaxseed proteins may be subjected to these methods. In another aspect, these proteins may include animal proteins such as chicken proteins, beef proteins, pork proteins, fish proteins, milk proteins, and egg proteins. In another aspect, the proteins may include fungal and microbial proteins.

In another aspect, the protein is an egg protein. These egg proteins may be from, for example, a bird species including chicken, duck, goose, pigeon, turkey, and partridge. In this aspect, the protein may include the transferrin family, ovalbumin, ovomucoid, lysozyme, or any combination thereof. In one aspect, the transferrin family includes ovotransferrin, lactoferrin, or hemoferrin. In this aspect, the egg protein may include ovotransferrin or various ovotransferrin isoforms. The ovotransferrin or ovotransferrin isoforms may be present in egg white, in whole egg, or in a liquid solution or a solid form (i.e. a powder form, gelatinous form, etc.). Due to its overall protein structure, ovotransferrin is generally thought to be resistant to hydrolytic cleavage (i.e. protease digestion). Ovotransferrin is a disulfide-rich single chain glycol-protein containing 686 residues with a molecular mass of about 78-80-kDa, and a glycan chain attached to the C-terminal domain. Ovotransferrin belongs to the transferrin family, which are two-lobe proteins (bilabial molecule) with a strong site for iron binding located in each lobe. It contains 15 disulfide bridges, and there are 6 homologous bridges in each half of the molecule and 3 extra bridges which occur only in the C-terminal half. These disulfide bridges are believed to play a role in ovotransferrin's resistance to enzymatic digestion. However, without wishing to be bound by theory, it is thought that ovotransferrin contains numerous bioactive peptides that may be useful in either inhibiting or reducing Angiotensin Converting Enzyme (ACE).

In certain aspects, by treating a protein with a reducing agent, a sonication step, a fermentation step, a heating step, a high pressure processing step, or any combination, as described above, the sulfhydral bonds or disulfide bridges may be cleaved thus rendering the protein more vulnerable to enzymatic hydrolysis or hydrolytic cleavage. In one aspect, the protein may be fermented by any microbe from which enzyme reductases are produced and subsequently reduce the disulfide bonds in the protein. For example, the microbe can be lactic acid bacteria. In another aspect, the protein can be in solution at 0.05 to 10% and can be heated at 65° C. to 120° C., 75° C. to 100° C., or 75° C. to 85° C. from 1 to 120 minutes, 5 to 50 minutes, or 10 to 20 minutes. In yet another aspect, the protein can be in solution to 0.05 to 10% and can be pressurized at 200-900 MPa for 1 to 300 minutes.

Reducing agents are substances that chemically reduce other substances by typically donating an electron or electrons and cleaving certain functional groups. In molecular assays, numerous reducing agents are known. In one aspect, the reducing agent can be a thiol compound. In this aspect, the thiol compound can cleave disulfide bonds in the protein. For example, β-mercaptoethanol, dithiothreitol (DTT), tris(2-carboxyethyl)phosphine (TCEP), and mercaptoethylamine are known reducing agents (i.e. thiol compounds) which aid in cleaving disulfide bonds and bridges. In one aspect, β-mercaptoethanol, dithiothreitol (DTT), tris(2-carboxyethyl) phosphine (TCEP), mercaptoethylamine, or any combination thereof may be used in this method. In another aspect, the reducing agent can be thioredoxin reductase, ferrous ion, lithium aluminum hydride ($LiAlH_4$), nascent hydrogen, $SO_2$, sodium amalgam, sodium borohydride ($NaBH_4$), stannous ion, and sulfite compounds.

In one aspect, the reducing agents may be added to a protein or a protein containing solution at an optimized concentration. In this aspect, about 2 mM to 2000 mM of the reducing agent may be added to a protein containing solution. For example, about 2 mM to 2000 mM of β-mercaptoethanol may be added to an ovotransferrin containing solution. In another example, about 2 mM to 2000 mM of DTT may be added to an ovotransferrin containing solution.

In yet another aspect, a sonication step, a high pressure processing step, a heating step, a fermentation step may be utilized either alone or in combination with the reducing agent. Each of these steps serves to alter overall protein structure through the cleavage or reduction of disulfide bonds. For example, when a sonication step is used in combination with a reducing agent, the sonication step can occur simultaneously with the introduction of the reducing agent to the protein containing solution or sequentially. For example, to further illustrate sequential steps, the reducing agent may be added and/or mixed with the protein containing solution and then subjected to the sonication step. The high pressure processing step, the heating step, or the fermentation step may each be used in a manner similar to the sonication step. In one aspect, when the sonication step is utilized in this method, it includes subjecting the protein or protein containing solution to 1 to 100 pulses at 20 kHz to 120 kHz, 40 kHz to 100 kHz, 50 kHz to 70 kHz, or about 60 kHz for a time period ranging from a few seconds to hours depending on reaction conditions (i.e. the amount of protein sample, disulfide bridge content, and various other conditions). In this aspect, the time period can range from 2 seconds to 600 minutes. The protein or protein containing solution can be exposed multiple times to sonication as needed (see Examples section as an example). In another aspect, prior to contacting protein or protein containing with the hydrolytic enzyme, the protein is sonicated followed by heating.

Without wishing to be bound by theory, after contacting the protein or protein containing solution with a reducing agent, a sonication step, or a combination thereof, chemical bonds thought to interfere with enzymatic hydrolysis, such as disulfide bridges, are cleaved by the reducing agent. With the disulfide bonds cleaved, the protein may be susceptible to enzymatic digestion or enzymatic cleavage. In this aspect, the protein may be contacted with a hydrolytic enzyme to produce the bioactive peptide. In one aspect, hydrolytic enzyme includes pepsin, thermolysin, trypsin, chymotrypsin, pancreatin, or any combination thereof. In another aspect, the hydrolytic enzyme includes at least two enzymes selected from the group comprising pepsin, thermolysin, trypsin, chymotrypsin, pancreatin, or any combination thereof. In yet another aspect, the hydrolytic enzyme is thermolysin, pepsin, or any combination thereof. In one aspect, the enzyme includes 0.005 to 5% (w/w, enzyme/substrate). In another aspect, the enzyme includes 0.05 to 2% (w/w, enzyme/substrate).

In certain aspects, the hydrolytic enzyme includes Protex 6L (alkaline serine endopeptidase, Genencor), Protex 7L (metallo neutral endopeptidase), Protex 26L (acid fungal endopeptidase), Protex 30L (bacterial alkaline serine endopeptidase), Protex 40L (subtilisin), Protex 50FP (acid fungal endo/exopeptidase complex), Protex 51FP (neutral fungal endo/exopeptidase complex), Protease A (thermolysin-enzyme complex), Protease M (aspergillopepsin I-enzyme complex), Protease N (bacillolysin-enzyme complex), Protease P (oryzin-enzyme complex), Protease S (bacillolysin-enzyme complex), and Acid protease II (rhizopupepsin-enzyme complex).

After contacting the protein with the hydrolytic enzyme, a hydrolysate is produced. The hydrolysate contains a mixture of two or more peptides, where one or more bioactive peptides of interest are present in the hydrolysate. After the hydrolysate is produced, the hydrolysate can be subjected to one or more purification steps in order to isolate bioactive peptides of interest. In one aspect, the hydrolysate can be fractionated to isolate individual bioactive peptides. For example, the hydrolysate can be subjected to a two-step fractionating procedure involving strong cation exchange chromatography on FPLC followed by reversed phase chromatography on HPLC (see Examples). By fractionating the different digestion products present in the hydrolysate, it is possible to isolate different bioactive peptides.

In certain aspects, prior to performing the methods described herein, the structure of bioactive peptides can be predicted by computational mapping. Such computational mapping may aid in developing reaction conditions (e.g. selection of reducing agent(s), hydrolytic enzyme(s), etc.) to selectively generate bioactive peptides. Computational mapping may further aid in predicting potent bioactive peptide fragments, which may be useful in treating a condition, inhibiting enzyme activity within a cell, or reducing enzyme activity within a cell. The Examples demonstrate how computational mapping can be used to identify bioactive peptides of interest.

In one aspect, these methods may be used to generate bioactive peptides which are 5, 10, 15, 20, 25, 30, 35, 40, 45, or 50 fold more potent than either the native protein or a protein only subjected to enzyme hydrolysis.

In another aspect, the antioxidant activity of bioactive peptides generated by these methods may be significantly greater than the antioxidant activity of either the native protein or a protein only subjected to enzyme hydrolysis. In this aspect, antioxidant activity may be quantified using at least three different methods including an Oxygen Radical Absorbance Capacity assay (ORAC), the DPPH Radical Scavenging Assay, and ABTS Radical Scavenging. In certain aspects, the bioactive peptides generated by the methods described herein have at least a 1, 2, 3, 4, 5, 6, 7, 8, 9, 10, 15, 20, 25, 30, 35, 40, 45, or 50 fold increase in antioxidant activity when compared to the protein or protein within the protein containing solution that was only subjected to enzyme hydrolysis. In one aspect, the bioactive peptide has an ORAC value greater than 5 μmol/μmol, 10 μmol/μmol, 15 μmol/μmol, or 20 μmol/μmol. The bioactive peptides produced herein have antioxidant properties comparable to known antioxidants (e.g., (+)-catechin has an ORAC value of 14.9 μmol/μmol). In one aspect, the bioactive peptide comprises the sequence WNI (SEQ ID NO:24). In another aspect, the bioactive peptide is GWNIP (SEQ ID NO:22) and GWNI (SEQ ID NO:23). These peptides were chemically synthesized based on structurally similar bioactive peptides derived from ovotransferrin (see Examples).

In one aspect, computational mapping may be utilized to predict potent bioactive peptides that may inhibit or reduce ACE activity. For example, Table 1 displays three predicted bioactive peptides derived from ovotransferrin, which include IRW (SEQ ID NO:1), IQW (SEQ ID NO:2), and LKP (SEQ ID NO:3). As stated above, ovotransferrin is generally thought to be resistant to hydrolytic cleavage. However, using the methods described herein, bioactive peptides may be generated from ovotransferrin. In this aspect, ovotransferrin may be contacted with a reducing agent, a sonication step, a high pressure processing step, a heating step, a fermentation step, or any combination thereof, as described above. Here, the sulfhydral bonds or disulfide bridges can be cleaved, which renders the protein more susceptible to enzymatic hydrolysis or hydrolytic cleavage. In this aspect, the ovotransferrin may then be contacted with thermolysin, pepsin, or a combination thereof. Peptide fragments, which may include bioactive peptides, can be further analyzed with a chromatography or mass spectrum step. For example, LC-MS/MS, LC-MS, or MS/MS may be used to evaluate the fragments generated from these methods (see FIG. 1). These fragments, which may include bioactive peptides, may be further compared to the computational map. In this aspect, if the predicted bioactive peptides are generated, these bioactive peptides may be further analyzed. This analysis may reveal enzyme inhibitory properties (e.g. ACE), increased antioxidant activity, or any combination thereof. Thus, the bioactive peptides can be used as a therapeutic to treat, reduce, or inhibit ACE, high blood pressure and/or diabetes in a subject. As stated above, the bioactive peptides described herein can be incorporated into foodstuffs, medication, or additional potable, ingestible, or edible compositions.

In one aspect, the protein is ovotransferrin and the bioactive peptide comprises the amino acid sequence SEQ ID NO:1, SEQ ID NO:2, SEQ ID NO:3, SEQ ID NO:10, or SEQ ID NO:23. Thus, in one aspect, the bioactive peptide comprises the amino acid sequence SEQ ID NO:1, SEQ ID NO:2, SEQ ID NO:3, SEQ ID NO:10, or SEQ ID NO:23.

The peptide disclosed herein can in some aspects be 3 to 6 amino acids in length. Thus, the bioactive peptide can be 3, 4, 5, 6, 7, 8, 9, 10, 11, 12, 13, 14, 15, 16, 17, 18, 19, or 20 amino acids in length.

Also disclosed herein is a hydrolysate produced by the herein disclosed methods of identifying and releasing bioactive peptides from their full length proteins. Also disclosed herein is a mixture of peptides purified from the hydrolysate produced by the herein disclosed methods. Also disclosed herein is a composition comprising a foodstuff, a medication, any potable, ingestible, or edible compositions comprising the hydrolysate or mixture of peptides purified from the hydrolysate produced by the herein disclosed methods. Also disclosed is a method of reducing or preventing high blood pressure in a subject comprising administering to the subject the hydrolysate or mixture of peptides purified from the hydrolysate produced by the herein disclosed methods. Also disclosed herein is a method for inhibiting or reducing the activity of angiotensin converting enzyme (ACE) comprising contacting a cell with the hydrolysate or mixture of peptides purified from the hydrolysate produced by the herein disclosed methods. Also disclosed herein is the use of the hydrolysate or mixture of peptides purified from the hydrolysate produced by the herein disclosed methods as an antioxidant.

Also disclosed herein is a composition comprising at least two different isolated peptides disclosed herein. For example, disclosed herein is a composition comprising at least two different isolated peptides, wherein each isolated peptide comprises an amino acid sequence selected from the group consisting of SEQ ID NO:1, SEQ ID NO:2, SEQ ID NO:3, SEQ ID NO:10, and SEQ ID NO:23. In some aspects, each of the at least two different isolated peptides are each 3 to 6 amino acids in length. Thus, also disclosed is a composition comprising at least two different isolated peptides, wherein each isolated peptide consists of the amino acid sequence SEQ ID NO:1, SEQ ID NO:2, SEQ ID NO:3, SEQ ID NO:10, or SEQ ID NO:23. In some aspects, one of the peptides in the mixture of peptides comprises the amino acid sequence SEQ ID NO:10 and one of the peptides in the mixture of peptides comprises the amino acid sequence SEQ ID NO:23. In some aspects, one of the peptides in the mixture of peptides consists of the amino acid sequence SEQ ID NO:10 and one of the peptides in the mixture of peptides consists of the amino acid sequence SEQ ID NO:23.

Also disclosed herein is a composition comprising a foodstuff, a medication, any potable, ingestible, or edible compositions comprising the at least two different isolated peptides disclosed herein. Also disclosed is a method of reducing or preventing high blood pressure in a subject comprising administering to the subject the at least two different isolated peptides disclosed herein. Also disclosed herein is a method for inhibiting or reducing the activity of angiotensin converting enzyme (ACE) comprising contacting a cell with the at least two different isolated peptides disclosed herein. Also disclosed herein is the use of the at least two different isolated peptides disclosed herein as an antioxidant.

Also disclosed herein is a method of reducing or preventing high blood pressure in a subject comprising administering to the subject an isolated peptide disclosed herein. For example, the isolated peptide can consist of the amino acid sequence SEQ ID NO:1, SEQ ID NO:2, SEQ ID NO:3, SEQ ID NO:10, SEQ ID NO:24. In some aspects of the method, the subject has diabetes.

Also disclosed herein is a method for inhibiting or reducing the activity of angiotensin converting enzyme (ACE) comprising contacting a cell with an isolated peptide disclosed herein. For example, the isolated peptide can consist of the amino acid sequence SEQ ID NO:1, SEQ ID NO:2, SEQ ID NO:3, SEQ ID NO:10, SEQ ID NO:23.

Also disclosed herein is an isolated nucleic acid comprising a sequence that encodes any one or more of the peptides disclosed herein. Thus, disclosed herein is an isolated nucleic acid comprising a sequence that encodes two or more peptides disclosed herein. Thus, disclosed herein is an isolated nucleic acid comprising a sequence that encodes two or more amino acid sequences selected from the group consisting of SEQ ID NO:1, SEQ ID NO:2, SEQ ID NO:3, SEQ ID NO:10, SEQ ID NO:23.

In one aspect, the bioactive peptides produced by the methods described herein can be chemically synthesized. For example, the bioactive peptides can be synthesized such that have an identical amino acid sequence as that of a bioactive peptide derived from a naturally-occurring protein (see e.g., Examples). In another aspect, the bioactive peptides may be further modified. In this aspect, the peptide can include an amino acid sequence at least about 90%, 80%, 70%, 66%, or 33%, or any percentage in between that represents a change, including an addition or deletion, of one or more amino acids.

As used herein in reference to a specified amino acid sequence, a conservative amino acid substitution refers to a sequence in which a first amino acid is replaced by another amino acid or amino acid analog having at least one biochemical property similar to that of the first amino acid. These similar biochemical properties include, for example, similar size, charge, hydrophilicity, hydrophobicity, or hydrogen-bonding capacity.

Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place.

Substantial changes in function or immunological identity are made by selecting substitutions that are less conservative, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains, acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. Specifically disclosed are variants of these and other proteins herein disclosed which have at least, 70% or 75% or 80% or 85% or 90% or 95% sequence identity to the stated sequence. Those of skill in the art readily understand how to determine the sequence identity of two peptides. For example, the homology can be calculated after aligning the two sequences so that the sequence identity is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is understood that there are numerous amino acid and peptide analogs which can be incorporated into the disclosed compositions. For example, there are numerous D amino acids or amino acids which have a different functional substituent. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way. D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations.

Molecules can be produced that resemble peptides, but which are not connected via a natural peptide linkage. For example, linkages for amino acids or amino acid analogs can include CH2NH—, —CH2S—, —CH2-CH2-, —CH=CH— (cis and trans), —COCH2-, —CH(OH)CH2-, and —CHH2SO. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

In yet another aspect, a nucleic acid sequence encoding the amino acid sequence of the bioactive peptide can be deduced. The nucleic acid sequence may include a chemically synthesized nucleic acid sequence, a naturally occurring nucleic acid sequence, or an isolated nucleic acid sequence. In this aspect the peptide may include an isolated nucleic acid having a sequence that encodes the bioactive peptide produced herein, or a conservative variant of each. In another aspect, the peptide may include an isolated nucleic acid consisting of a sequence that encodes any of the bioactive peptides described herein. In certain aspects, the nucleic acid sequence encoding the bioactive peptide can be cloned into vectors including plasmids and viral vectors and further expressed in bacteria and subsequently isolated. The entire gene fragment which encodes the bioactive peptide can be cloned into a vector and subsequently expressed in bacterial cells. In another aspect, the nucleic acid sequence encoding the bioactive peptide can be gene fragments. These gene fragments which encode the bioactive peptide can be used to create a recombinant fusion gene and can be subsequently expressed in bacterial cells. In each of these aspects, a peptide fragment having a bioactive peptide produced herein can be isolated and subjected to the methods described herein.

The provided polypeptide can further constitute a fusion protein or otherwise have additional N-terminal, C-terminal, or intermediate amino acid sequences, e.g., linkers or tags.

"Linker", as used herein, is an amino acid sequences or insertion that can be used to connect or separate two distinct polypeptides or polypeptide fragments, wherein the linker does not otherwise contribute to the essential function of the composition. A polypeptide provided herein, can have an amino acid linker comprising, for example, the amino acids GLS, ALS, or LLA. A "tag", as used herein, refers to a distinct amino acid sequence that can be used to detect or purify the provided polypeptide, wherein the tag does not otherwise contribute to the essential function of the composition. The provided polypeptide can further have deleted N-terminal, C-terminal or intermediate amino acids that do not contribute to the essential activity of the polypeptide.

The disclosed composition can be linked to an internalization sequence or a protein transduction domain to effectively enter the cell. Recent studies have identified several cell penetrating peptides, including the TAT transactivation domain of the HIV virus, antennapedia, and transportan that can readily transport molecules and small peptides across the plasma membrane. More recently, polyarginine has shown an even greater efficiency of transporting peptides and proteins across the plasma, membrane making it an attractive tool for peptide mediated transport. Nonaarginine has been described as one of the most efficient polyarginine based protein transduction domains, with maximal uptake of significantly greater than TAT or antennapeadia. Peptide mediated cytotoxicity has also been shown to be less with polyarginine-based internalization sequences. Nonaarginine mediated membrane transport is facilitated through heparan sulfate proteoglycan binding and endocytic packaging. Once internalized, heparan is degraded by heparanases, releasing Nonaarginine which leaks into the cytoplasm. Studies have recently shown that derivatives of polyarginine can deliver a full length p53 protein to oral cancer cells, suppressing their growth and metastasis, defining polyarginine as a potent cell penetrating peptide.

Thus, the provided polypeptide can comprise a cellular internalization transporter or sequence. The cellular internalization sequence can be any internalization sequence known or newly discovered in the art, or conservative variants thereof. Non-limiting examples of cellular internalization transporters and sequences include Polyarginine (e.g., Nonaarginine), Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol). Any other internalization sequences now known or later identified can be combined with a peptide disclosed herein.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

I. Prediction of Potent Bioactive Peptides

Preparation of Dataset

Egg white (Lysozyme, ovotransferrin, ovalbumin, ovomucin and ovomucoid) and egg yolk protein (High density lipoprotein, low density lipoprotein, Phosvitin and livetin) sequences were obtained from the public database, National Center for Biotechnology Information (NCBI) protein database (http://www.ncbi.nlm.nih.gov).

In silico Protein Digestion and Activity Prediction

In silico digestion of these protein sequences were performed by the software Peptidecutter, available in Expasy molecular biology server (http://ca.expasy.org/tools/peptidecutter), using several enzymes (present in Expasy) individually and in combination. The enzymes were chymotrypsin (low specificity), pepsin (pH 1.3), pepsin (pH>2), trypsin, and thermolysin. These enzymes were also used to make various combinations; such combinations included combination I (chymotrypsin (high specificity), pepsin (pH1.3), trypsin); combination II (chymotrypsin (high specificity), trypsin); combination III [pepsin (pH1.3), chymotrypsin (high specificity)]; combination IV [pepsin (PH1.3), trypsin]; combination V (thermolysin, protein kinasek); combination VI (trypsin, thermolysin); combination VII [thermolysin, pepsin (PH1.3)]; combination nI [Trypsin, Pepsin (pH>2)]; combination nII [thermolysin, pepsin (pH>2)]; combination nIII [chymotrypsin(low), pepsin (pH>2) & trypsin]; and combination nIV [thermolysin, chymotrypsin(low specificity)].

More than 20,000 peptides were generated from 75 in-silico digestions. After the stimulated digestion, the activities of the resulting peptides were predicted according to our models using the SIMCA-P version +11 (Umetrics INC, Kinnelon, N.J.) (See Wu, J., Aluko, R. E., Nakai, S. Structural requirement of angiotensin converting enzyme inhibitory peptides: quantitative structure-activity relationships of di- and tri-peptide. *Journal of Agricultural and Food Chemistry* 54, 732-738, hereby incorporated by reference in its entirety). Their $IC_{50}$ values were predicted by QSAR models and ovotransferrin digest by a combination of thermolysin and pepsin showed several potent novel peptides. The most potent predicted peptides are illustrated in Table 1.

TABLE 1

Most potent peptides predicted in ovotransferrin hydrolysate.

| Predicted peptides | SEQ ID NO | $IC_{50}$ (µM) | Enzyme combination |
|---|---|---|---|
| IRW | SEQ ID NO: 1 | 0.6 | Thermolysin-Pepsin |
| IQW | SEQ ID NO: 2 | 1.4 | Thermolysin-Pepsin |
| LKP | SEQ ID NO: 3 | 2.8 | Thermolysin-Pepsin |

In-vitro Digestion

Two conditions were chosen to produce protein hydrolysates suspected to contain potent ACE inhibitory peptides predicted from the computation study described above. All of the in vitro digestions were carried out through Titrando for maintaining constant pH during the course of the hydrolysis. The temperature of the sample was maintained constantly by a hot plate or water bath with a stirrer. Ovotransferrin was first hydrolyzed by thermolysin as conditions listed in Table 2; after 3 hr hydrolysis, the pH was reduced to 1.3 by adding 2N HCl solution and lowered the temperature to 37° C. for addition 3 hr hydrolysis by pepsin at pH 1.3. The hydrolysis was terminated by raising the temperature to 95° C. and kept it for 10 minutes; the samples were centrifuged at 10000 g (i.e. RPMs) for 30 min at 4° C. and the supernatants were collected and freeze dried for further analysis.

TABLE 2

Recommended pH and temperature of enzymes

| Enzyme | pH | Temperature |
|---|---|---|
| Pepsin | 1.3 and 3 | 37° C. |
| Thermolysin | 8 | 55° C. |
| Trypsin | 7.6 | 25° C. |
| Chymotrypsin | 7.8 | 25° C. |
| Pancreatin | 8 | 50° C. |

Identification of Peptides

Identification of the predicted peptides in expected samples were carried out by liquid chromatography tandem mass spectrometry (LC-MS/MS). The analysis was carried out in Waters (Micromass) Q-TOF Premier with a C18 column Samples wash with 0.1% formic acid, to create an acidic environment; followed by 99% water and 1% acetonitrile to wash any excess amount of salts. Samples then analyzed in liquid chromatography and ionization was done by Electrospray ionization technique (ESI). Then the peptide mass were detected through Q-TOF analyzer. All analyses were performed using an injection volume of 10 µL.

II. Investigation of Ace Inhibitory Activity

ACE Inhibitory Activity of Ovotransferrin Hydrolysate without Reducing Agent Treatment In vitro ACE inhibitory activity was measured. See Cushman, D. W.; Cheung, H. S. Spectrophotometric assay and properties of angiotensin-converting enzyme of rabbit lung. *Biochemical Pharmacology* 1971, 20, 1637-48; which is hereby incorporated by reference in its entirety.

As shown in Table 3, ovotransferrin hydrolysates prepared by thermolysin and pepsin individually and in combination did not show very potent in vitro activity. Predicted peptides were not identified in the ovotransferrin hydrolysate by LC-MS/MS. However, the predicted peptide sequences were observed in MS/MS spectrum, adjoining with some other amino acids. This result indicated that the predicted peptides had not been released from its parent protein, ovotransferrin.

TABLE 3

ACE inhibitory activity of the Ovotransferrin hydrolysate without reducing agents treatments.

| Ovotransferrin hydrolysate | $IC_{50}$ (µg/mL) |
|---|---|
| Thermolysin | 215.0 ± 3.39 |
| Pepsin | 320.0 ± 5.16 |
| Both | 198.0 ± 1.21 |

ACE Inhibitory Activity of Ovotransferrin Hydrolysate with Reducing Agent Treatment As described above, in vitro ACE inhibitory activity was measured. It was previously reported that ovotransferrin contains 15 disulphide bridges. The effects of sonication (60 kHz, for 2 mins by 4 pulses) and reducing agents (β-mercaptoethanol at 10 mM or dithiothreitol (DTT) at 5 mM) on the activity of hydrolysate were studied. Prior to hydrolysis, ovotransferrin solution was treated by sonication or by reducing agent; further hydrolysis was carried out as in vitro digestion.

Ovotransferrin was treated by ultra-sonication, β-mercaptoethanol, or DTT respectively, prior to enzymatic hydrolysis. As shown in Table 4, activity of the ultrasonication and reducing agent treated hydrolysate was increased 20-fold, compared to the control (under the same enzymatic hydrolysis but without sonication and reducing agent treatment). The hydrolysate is the most potent hydrolysate that was ever reported; since the composition of peptides is mainly small peptides, the hydrolysate could be applied directly for functional food product development.

TABLE 4

ACE inhibitory activity of the Ovotransferrin hydrolysate with three different kinds of reducing agents treatments.

| Ovotransferrin hydrolysate | $IC_{50}$ (µg/mL) |
| --- | --- |
| Control | 198.0 ± 1.21 |
| Sonication | 9.2 ± 3.11 |
| Beta-mercaptoethanol | 45.6 ± 8.41 |
| DTT | 10.7 ± 2.62 |

This hydrolysate was further analyzed by LC-MS/MS and the two most potent, predicted peptides were also identified. LC-MS spectra of the hydrolysate sample and MS/MS spectrum of the predicted potent peptides were illustrated at FIG. 1.

II. Investigation of Antioxidant Activity

Materials

Egg ovotransferrin (Ovotransferrin 100) was obtained from Neova technologies (Abbotsford, BC, Canada). Thermolysin, 2,2'-azobis(2-methylpropionamidine)dihydrochloride (AAPH), 2,2-diphenyl-1-picrylhydrazyl (DPPH), 2,2'-azinobis(3-ethylbenzothiazoline-6-sulfonic acid) (ABTS), 6-hydroxy-2,5,7,8-tetramethylchroman-2-carboxylic acid (Trolox), bovine serum albumin, sodium hydroxide and formic acid were obtained from Sigma Canada (Oakville, ON, Canada). Ammonium acetate, ammonium carbonate, HPLC-grade acetonitrile, fluorescein, potassium monobasic phosphate, hydrochloric acid and trifluoroacetic acid (TFA) were obtained from Fisher Scientific Canada (Ottawa, ON, Canada). Synthetic peptides (>95% purity) used in the study were commercially obtained from Genscript (Piscataway, N.J.).

Sample Preparation 20 g of ovotransferrin was dispersed in Millipore water to make 5% (w/v) slurry. The slurry was sonicated at 60 Hz by Sonic 300 (Systems Corporation, NY) for four 30-s pulses, at 1-s intervals. After heating the slurry at 80° C. in a water bath for 15 min, the protein solution was cooled down to 60° C. and adjusted to pH 8. 100 mg of thermolysin was added into the protein solution to start a digestion. The temperature and pH was maintained constantly by a water bath and a Brinkmann Titrando 842 (Brinkmann Instrument Inc., Mississauga, ON, Canada) respectively during the digestion. After 3 h, the enzymatic reaction was terminated by lowering the pH to 4.5 with 2 M HCl. The hydrolysate was separated by centrifugation at 10,000×g for 30 min at 4° C. The supernatant was ultrafiltered by membrane with MWCO 3 kDa (Millipore, Billerica, Mass.) and the permeate obtained was stored at 4° C. for subsequent FPLC fractionation.

Cation Exchange Chromatography

The permeate was loaded onto a HiPrep 16/10 SP FF column (16×100 mm, 90 µm, GE Healthcare, Sweden) operated by an AKTA explorer 10S system and eluted using 10 mM ammonium acetate pH 4.0 (buffer A) and 0.5 M ammonium carbonate (buffer B) from 0 to 8% B over 8 column volumes at a flow rate of 5 mL/min. The elution was monitored at 280 nm and fractions were collected, and freeze-dried for the peptide content and the ORAC assay.

Reversed Phase Chromatography

The active fractions from the above cation exchange chromatography were further fractionated by a Waters XBridge C18 column (10 mm×150 mm, 5 µm) eluted by acetonitrile containing 0.1% trifluoroacetic acid (mobile phase B) from 2 to 32% at a flow rate of 5 mL/min. The elution was detected at 220 nm and fractions were collected every 2 min by a stand-alone fraction collector semi-controlled by Empower 2 software, concentrated using a rotary evaporator, and analyzed for the peptide content and the ORAC assays.

Peptide Content Assay

The peptide content was measured by use of OPA reagent solution (Pierce 26025). 40 µL of each sample including bovine serum albumin (BSA) standards (0-1 mg/mL) was mixed with 100 µL of the OPA reagent solution in microplate wells. The microplate was immediately placed in a Fluoroskan Ascent microplate reader (Thermo Electron Corporation, Waltham, Mass.) with 355-P excitation and 460-P emission filters and the fluorescence was recorded. The peptide concentration was calculated based on a standard curve derived from BSA standard solutions and expressed in units of µg/mL.

ORAC-FL Assay

Briefly, 80 mM AAPH and 200 nM fluorescein in 75 mM phosphate buffer at pH 7.4 were prepared for each experiment. For each run, 20 µL of antioxidant, and 80 µL of phosphate buffer (or 100 µL of Trolox standard solutions at final concentrations of 1 to 8 µM) were placed in wells of a 96-well microplate, followed by addition of 50 µL of the fluorescein solution. The mixture was preincubated for 15 min at 37° C. 50 µL of AAPH solution was added rapidly using a multichannel pipet. The microplate was immediately placed in a Fluoroskan Ascent microplate reader (Thermo Electron Corporation) with 485-P excitation and 538-P emission filters and the fluorescence recorded every minute for 100 min. All readings were recorded using Fluoroskan Ascent software. The area under the curve of fluorescence decay (AUC) was calculated using Graphpad prism software (trial version). Regression equations between AUC and antioxidant concentrations were calculated for all the samples. The ORAC value was calculated by dividing the slope of sample regression curve by the slope of Trolox regression curve. Final ORAC values were expressed as µmol of Trolox equivalent/mg of protein or peptide.

Analysis by Online RP-UPLC-MS/MS

Identification of peptides in two most active fractions from the RP-HPLC separation was carried out by a Waters ACQUITY UPLC system connected online to a Waters Micromass Q-TOF Premier Instrument (Milford, Mass.). The samples were separated on a Waters Atlantis dC18 (75 µm×150 mm, 3 µm) UPLC column by using solvent A (0.1% formic acid in water) and solvent B (0.1% formic acid in aceonitrile). 5 µL of sample was injected to a 5 µm trapping column and trapped for 2 min at a flow rate of 10 µL/min using 99% solvent A, followed by a gradient from 99% A to 90% A over 5 min, to 70% A over 30 min, to 60% over 3 min and to 5% A over 1 min at a constant flow rate of 0.350 µL/min. The flow rate was increased to 0.500 µL/min, held at 5% A for 2 min, increased to 98% A over 1 min, held for another 27 min, and then decreased to 0.350 µL/min over 1 min. The flow entered directly into the mass spectrometer via a nanoLockspray ionization source in a positive ion mode (capillary voltage 3.80 kV and a source temperature of 100° C.). Spectra were recorded over the mass/charge (m/z) range of 100-1000 in MS mode and 50-1500 in MS/MS mode. The signal threshold to perform auto MS/MS in the data-dependent acquisition was 20 counts per second in total ion current and the precursor ions were isolated within a range of 3.0 m/z. Instrumental control and data analysis were performed using the MassLynx software (Micromass UK Ltd., Wythenshawe, Manchester, UK). Peaks Viewer 4.5 (Bioinformatics Solutions Inc., Waterloo, ON, Canada) was used in combination with manual de novo sequencing to process the MS/MS data and to perform peptide sequencing.

Statistical Analysis

All data was analyzed by SAS version 9.0 (SAS Institute, Cary, N.C.) software using one-way ANOVA analysis and the values were ranked by Duncan grouping.

Fractionation and Characterization of Antioxidant Peptides

Figure 2:
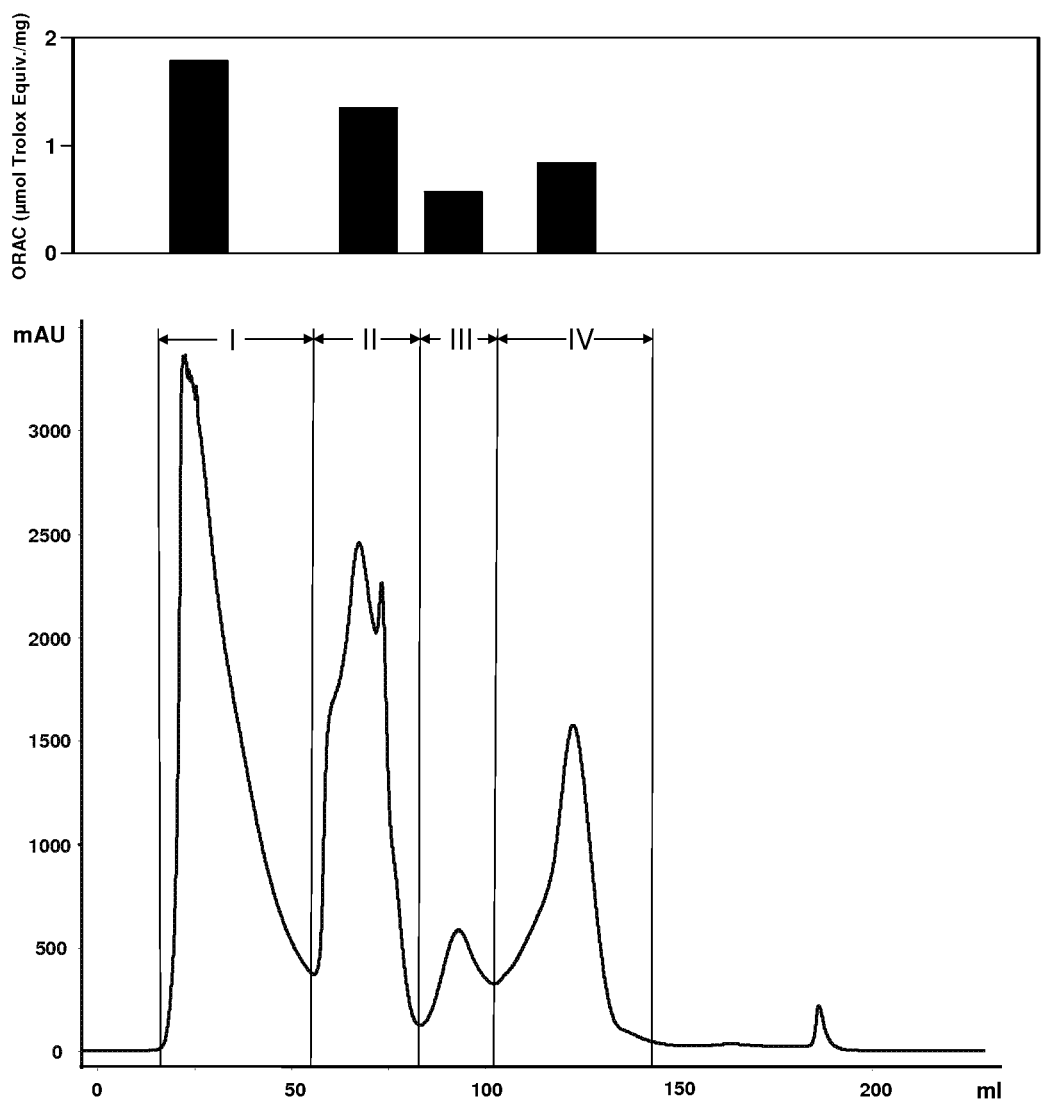
FIG. 2 shows fractionation by FPLC of the 3-kD permeate obtained from ovotransferrin by thermolysin. Collected fractions are labeled using the Roman Numerals (I, II, III and IV). ORAC-FL values of the fractions are represented by the histogram in the upper panel.
Figure 3:
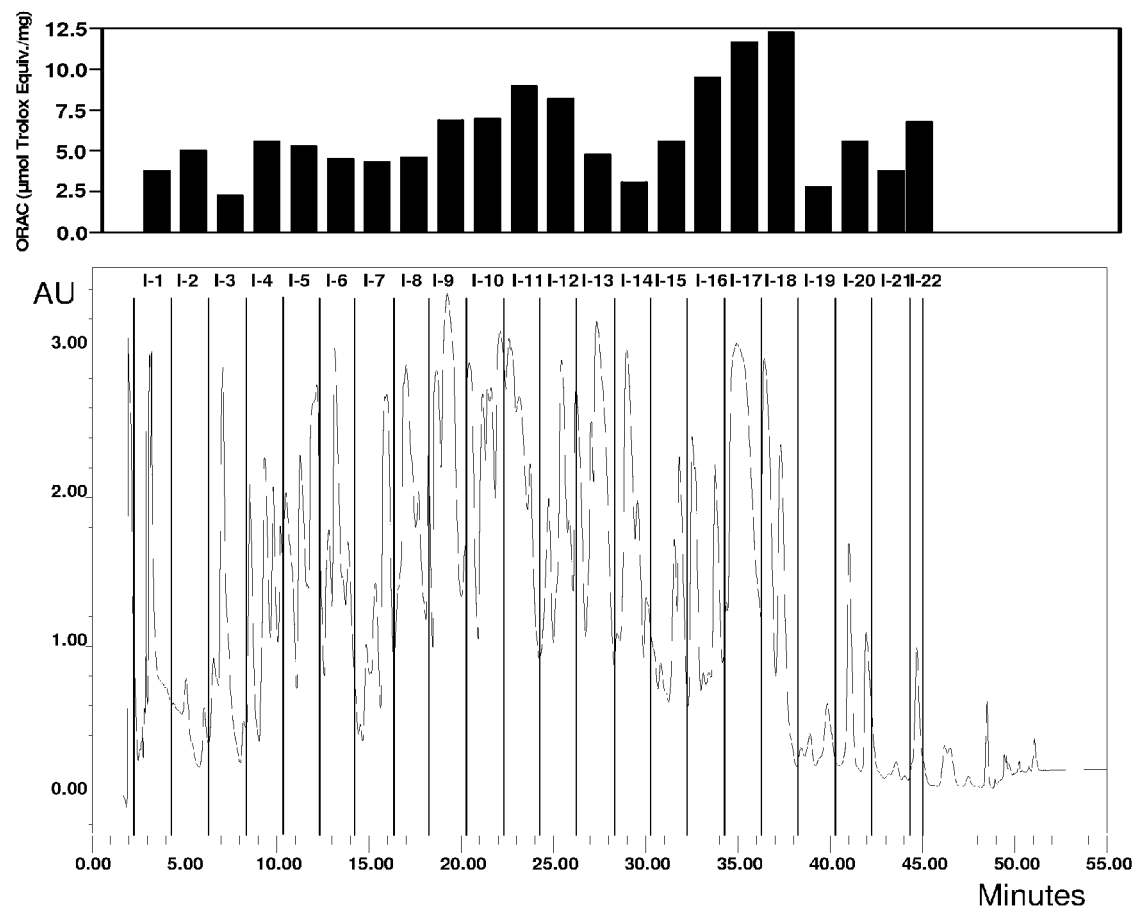
FIG. 3 shows fractionation by preparative RP-HPLC of the active fractions from FPLC: (A) Fraction I and (B) Fraction II. ORAC-FL values of the fractions are represented by the histogram in the upper panel.

The 3-kDa permeate from ovotransferrin hydrolysate digested by thermolysin was subjected to a two-step fractionating procedure, involving strong cation exchange chromatography on FPLC followed by reversed phase chromatography on HPLC. Four fractions were collected from the cation exchange chromatography, as shown in FIG. 2. Peptides contained in the first two eluting peaks (Fractions I and II) had higher antioxidant activity than those in the later eluting peaks (Fractions III and IV) and the crude 3-kDa permeate. In agreement with previous reports (28-30), acidic fraction (Fraction I) obtained from cation exchange chromatography exhibited higher activity than neutral or basic fractions. The two active fractions (I and II) were further separated by reversed phase chromatography, as shown in FIG. 3. Both fractions showed quite complex peak profiles in the chromatograms. Consistent with the fact that Fraction I had a slightly higher ORAC value than Fraction II, subfractions from Fraction I (I-1 to I-22) were shown to have higher ORAC values than subfractions from Fraction II (II-1 to II-19) in general. 17 out of 22 subfractions from Fraction I had ORAC values above 4.0 µmol Trolox equivalent/mg while 9 out 19 subfractions from Fraction II had ORAC values higher than or as high as 4.0 µmol Trolox equivalent/mg. Among them, I-17 and I-18 were the most two fractions, with their ORAC values being 11.7 and 12.3 µmol/mg, respectively. Therefore, most fractions obtained from the RP-HPLC had much higher ORAC values than the fractions obtained from the pepsin hydrolysate of crude egg white in a previous study (all fractions gave an ORAC value lower than 4.0 µmol Trolox equivalent/mg).

To identify the most potent peptides in the acquired fractions, Fractions I-17 and I-18 were further characterized by LC/MS/MS. Sixteen peptides have been identified in total and listed in Table 5. Among them, fourteen originated from ovotransferrin and two from ovalbumin, the most possible contaminating protein in the ovotransferrin product. Two b ions (m/z 542.2 and 469.2) were identified, corresponding to the $(M+H)^+$ ions of peptides AGWNI (SEQ ID NO:9) and ILEL (SEQ ID NO:18) after water loss, respectively. C-terminal addition of Pro rendered the observation of complete $(M+H)^+$ ions for peptides AGWNIP (SEQ ID NO:8) (m/z 657.3) and ILELP (SEQ ID NO:17) (m/z 584.3). All fourteen peptides originating from ovotransferrin were chemically synthesized and their antioxidant activities measured. The majority of the identified peptides showed high ORAC values greater than 3 µmol TE/µmol. Two peptides, LSKAQSDFG (SEQ ID NO:13) and LVEKGDVAFI (SEQ ID NO:16), had negative ORAC values, suggesting that they have prooxidant activity. Some peptide fractions from protein hydrolysates have been shown to be prooxidative.

A tetrapeptide WNIP (SEQ ID NO:10) showed the highest ORAC value (15.47 µmol/µmol). Compared to known antioxidants of plant origin, this activity was close to that of (+)-catechin (14.9 µmol/µmol), measured under the same conditions. To examine how the context of the peptide fragment embedded in the protein sequence affected its antioxidant activity, two more structurally related peptides, GWNIP (SEQ ID NO:22) and GWNI (SEQ ID NO:23), were synthesized and tested by the ORAC assay. The fact that GWNI (SEQ ID NO:23) and WNIP (SEQ ID NO:10) had similar ORAC values (15.47 µmol/µmol vs. 13.90 µmol/µmol) indicated that WNI (SEQ ID NO:24) might be the core motif responsible for their high antioxidant activity. Addition of Ala to the N-terminus of GWNI (SEQ ID NO:23) (to make AGWNI (SEQ ID NO:9)) or addition of either Gly or Ala-Gly to the N-terminus of WNIP (SEQ ID NO:10) (to make GWNIP (SEQ ID NO:22) or AGWNIP (SEQ ID NO:8)) decreased the antioxidant activity by half (Table 6). C-terminal extension of the peptide AGWNIP (SEQ ID NO:8) (to AGWNIPIGT (SEQ ID NO:7)) did not decrease the antioxidant activity further.

TABLE 5

| SEQ NO | m/z | $q^a$ | obsd mass | calcd mass$^b$ | peptide sequence | ovotransferrin fragment |
|---|---|---|---|---|---|---|
| 4 | 996.4 | 2 | 1991.8 | 1991.92 | IA(deaminationN)NEADAISLDGGQVFEAG | f(68-87) |
| 5 | 935.9 | 2 | 1870.8 | 1870.83 | PIAAEVYE(OxH)TEGSTTSY | f(95-111) |
| 6 | 879.4 | 2 | 1757.8 | 1757.79 | IAAEVYEHTEGSTTSY | f(96-111) |
| 7 | 928.3 | 1 | 928.3 | 928.49 | AGWNIPIGT | f(142-150) |
| 8 | 657.3 | 1 | 657.3 | 657.34 | AGWNIP | f(142-147) |
| 9 | 542.2 | 1 | 542.2 | 542.27 | AGWNI (b ion) | f(142-146) |
| 10 | 529.2 | 1 | 529.2 | 529.28 | WNIP | f(144-147) |
| 11 | 802.8 | 2 | 1604.6 | 1604.74 | AIEWEGIESGSVEQA | f(156-170) |
|  | 813.8 | 2 |  |  | AIEWEGIESGSVEQA monosodium adduct |  |
| 12 | 767.3 | 2 | 1533.6 | 1533.71 | IEWEGIESGSVEQA | f(157-170) |
| 13 | 953.4 | 1 | 953.4 | 952.47 | LSKAQSDFG | f(286-294) |
| 14 | 628.3 | 1 | 628.3 | 628.30 | LGFEY | f(339-343) |

TABLE 5-continued

| SEQ NO | m/z | q[a] | obsd mass | calcd mass[b] | peptide sequence | ovotransferrin fragment |
|---|---|---|---|---|---|---|
| 15 | 791.3 | 1 | 791.3 | 791.36 | LGFEYY | f(339-344) |
| 16 | 545.8 | 2 | 1090.6 | 1090.61 | LVEKGDVAFI | f(550-559) |
|  |  |  |  |  |  | ovalbumin fragment |
| 17 | 584.3 | 1 | 584.3 | 584.37 | ILELP | f(230-234) |
| 18 | 469.2 | 1 | 469.2 | 469.30 | ILEL (b ion) | f(230-233) |

[a]Charge state of the precursor ion.
[b]Monoisotopic mass.

TABLE 6

| SEQ NO | Peptide Sequence | aa's | MW | pI | ORAC (µmol/µmol) |
|---|---|---|---|---|---|
| 19 | IANNEADAISLDGGQVFEAG | 20 | 1991.08 | 3.43 | 0.43 ± 0.05 |
| 20 | PIAAEVYEHTEGSTTSY | 17 | 1854.93 | 4.24 | 1.68 ± 0.03 |
| 6 | IAAEVYEHTEGSTTSY | 16 | 1757.81 | 4.24 | 2.39 ± 0.17 |
| 7 | AGWNIPIGT | 9 | 928.05 | 5.57 | 5.25 ± 0.26 |
| 8 | AGWNIP | 6 | 656.73 | 5.57 | 7.64 ± 0.83 |
| 9 | AGWNI | 5 | 559.62 | 5.57 | 8.55 ± 0.60 |
| 10 | WNIP | 4 | 528.60 | 5.52 | 15.47 ± 0.68 |
| 11 | AIEWEGIESGSVEQA | 15 | 1604.70 | 3.58 | 0.95 ± 0.46 |
| 12 | IEWEGIESGSVEQA | 14 | 1533.60 | 3.58 | 0.73 ± 0.16 |
| 13 | LSKAQSDFG | 9 | 952.02 | 5.84 | -1.40 ± 0.69 |
| 14 | LGFEY | 5 | 627.69 | 4.00 | 9.79 ± 0.55 |
| 15 | LGFEYY | 6 | 790.56 | 4.00 | 7.25 ± 0.71 |
| 21 | VIPMGL | 6 | 628.83 | 5.49 | 2.89 ± 0.15 |
| 16 | LVEKGDVAFI | 10 | 1090.27 | 4.37 | -0.07 ± 0.03 |
| 22 | GWNIP | 5 | 585.65 | 5.52 | 6.19 ± 0.64 |
| 23 | GWNI | 4 | 488.54 | 5.52 | 13.90 ± 1.05 |

As shown in Table 7, enzymatic hydrolysis of ovotransferrin could increase the antioxidant activity over 5-fold, compared to un-hydrolyzed ovotransferrin. In contrast to the ACE inhibitory activity, sonication or reducing agent treatments did not affect the antioxidant activity, with the exception of thermolysin hydrolysate.

TABLE 7

ORAC values of ovotransferrin hydrolysates

| Ovotransferrin hydrolysate | ORAC (µmol/mg) |
|---|---|
| Unhydrolyzed ovotransferrin | 0.21 ± 0.04 |
| thermolysin without sonication | 0.49 ± 0.01 |
| thermolysin with sonication | 1.95 ± 0.02 |
| pepsin without sonication | 1.42 ± 0.05 |
| pepsin with sonication | 1.67 ± 0.06 |
| thermolysin + pepsin without sonication | 1.14 ± 0.04 |
| thermolysin + pepsin with sonication | 1.53 ± 0.03 |
| thermolysin + pepsin with 2-ME | 1.44 ± 0.02 |
| thermolysin + pepsin with DTT | 1.56 ± 0.04 |

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A hydrolysate composition produced by the method comprising
   (a) contacting chicken egg ovotransferrin or a protein containing chicken egg ovotransferrin with a reducing agent, subjecting the chicken egg ovotransferrin or a protein containing chicken egg ovotransferrin to a sonication step, or a combination thereof; and
   (b) sequentially contacting the chicken egg ovotransferrin or a protein containing chicken ovotransferrin after step (a) with (1) thermolysin then pepsin or (2) pepsin then thermolysin to produce the hydrolysate composition, wherein the hydrolysate composition comprises at least one peptide selected from the group consisting of SEQ ID NO:1 and SEQ ID NO:2.

2. A mixture of peptides purified from the hydrolysate composition of claim 1.

3. A composition comprising a foodstuff, a medication, any potable, ingestible, or edible compositions comprising the hydrolysate composition of claim 1.

4. A method of reducing high blood pressure in a subject comprising administering to the subject the hydrolysate composition of claim 1.

5. The method of claim 4, wherein the subject has diabetes.

6. A method for inhibiting or reducing the activity of angiotensin converting enzyme (ACE) comprising contacting a cell with the hydrolysate composition of claim 1.

7. A composition comprising a foodstuff, a medication, any potable, ingestible, or edible compositions comprising the hydrolysate composition of claim 1.

8. A method of reducing high blood pressure in a subject comprising administering to the subject the hydrolysate composition of claim 1.

9. The method of claim 8, wherein the subject has diabetes.

10. A method for inhibiting or reducing the activity of angiotensin converting enzyme (ACE) comprising contacting a cell with the hydrolysate composition of claim 1.

11. A peptide selected from the group consisting of SEQ ID NO:1 and SEQ ID NO:2.

12. A composition comprising a foodstuff, a medication, any potable, ingestible, or edible compositions comprising the peptide of claim 11.

13. A method of reducing high blood pressure in a subject comprising administering to the subject the peptide of claim 11.

14. The method of claim 13, wherein the subject has diabetes.

15. A method for inhibiting or reducing the activity of angiotensin converting enzyme (ACE) comprising contacting a cell with the peptide of claim 11.

16. A composition comprising a foodstuff, a medication, any potable, ingestible, or edible compositions comprising the peptide of claim 11.

17. A method of reducing high blood pressure in a subject comprising administering to the subject the peptide of claim 11.

18. The method of claim 17, wherein the subject has diabetes.

19. A method for inhibiting or reducing the activity of angiotensin converting enzyme (ACE) comprising contacting a cell with the peptide of claim 11.

* * * * *